United States Patent [19]

Lindmayer et al.

[11] Patent Number: 4,518,385

[45] Date of Patent: May 21, 1985

[54] DISPOSABLE SYRINGE FOR NEEDLELESS INJECTOR

[75] Inventors: Istvan Lindmayer, Pierrefonds; Raymond M. Grunwald, Dollard des Ormeaux, both of Canada

[73] Assignee: Preci-Tech Ltd., Ville St. Laurent, Canada

[21] Appl. No.: 503,765

[22] Filed: Jun. 13, 1983

[51] Int. Cl.³ .............................................. A61M 11/00
[52] U.S. Cl. .................................... 604/68; 604/414; 141/2
[58] Field of Search ...................... 604/68, 70, 71, 72, 604/218, 411–415; 141/2

[56] References Cited

U.S. PATENT DOCUMENTS

| | | | |
|---|---|---|---|
| 2,800,903 | 7/1957 | Smoot | 604/68 |
| 3,115,133 | 12/1963 | Morando | 604/70 |
| 3,945,383 | 3/1976 | Bennett et al. | 604/72 |

FOREIGN PATENT DOCUMENTS

| | | | |
|---|---|---|---|
| 958355 | 3/1950 | France | 604/218 |
| 1212753 | 11/1970 | United Kingdom | 604/218 |

Primary Examiner—John D. Yasko

[57] ABSTRACT

A disposable syringe for use in a needleless hypodermic injector includes a transparent, plastic barrel with an injection orifice in a closed front end thereof and an open rear end for receiving a plunger. The barrel is filled with medicine using a needle, which may be integral with the barrel, by partially withdrawing the plunger from the barrel to suck medicine through the injection orifice. The barrel and plunger are placed in an injector and the injector is actuated to push the plunger into the barrel, discharging the medicine. Alternatively, the syringe is filled with medicine while in an injector of the type which includes a removable injection head and a removable charging or filling head.

12 Claims, 8 Drawing Figures

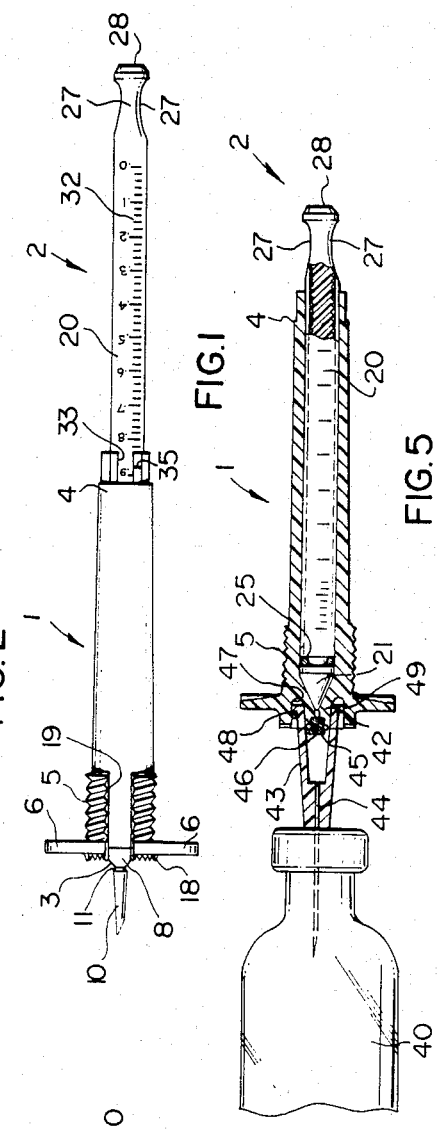

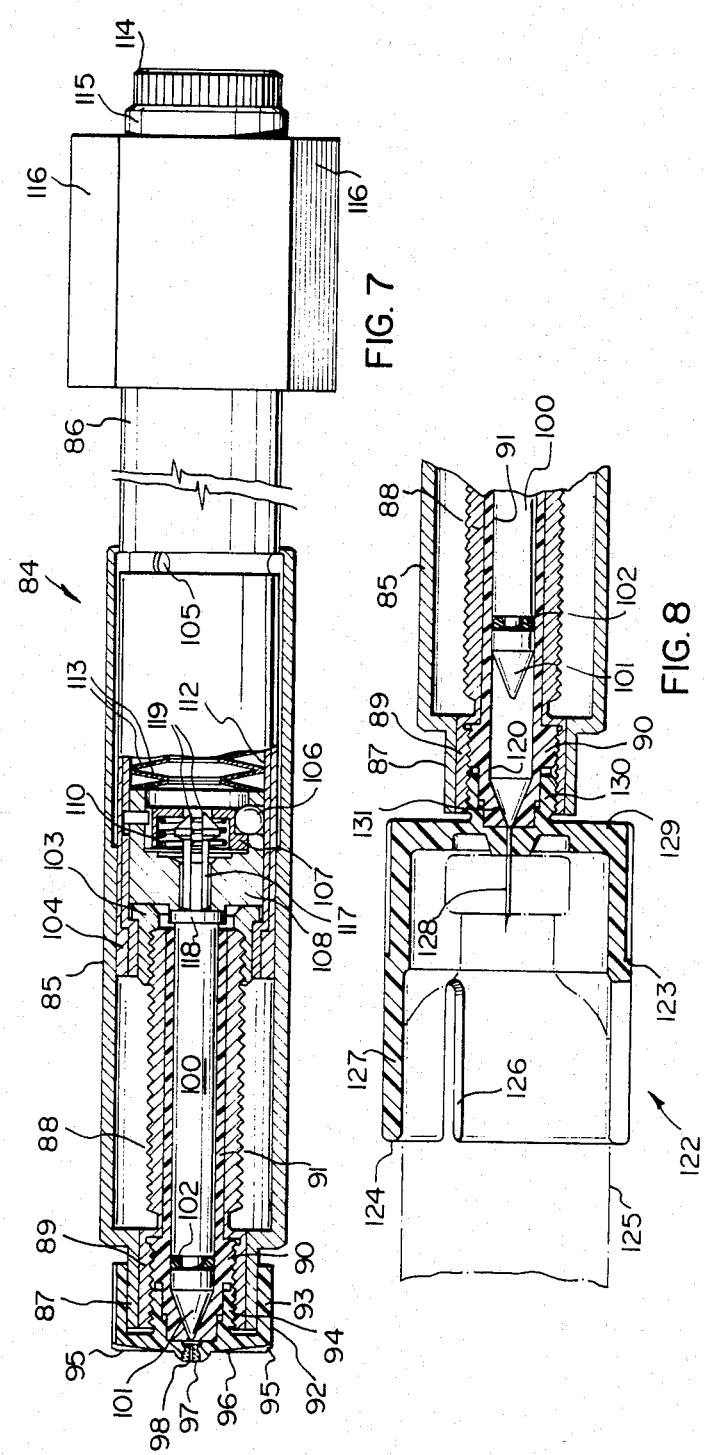

DISPOSABLE SYRINGE FOR NEEDLELESS INJECTOR

BACKGROUND OF THE INVENTION

1. Field of the Invention

This invention relates to a syringe, and in particular to a syringe for use with a needleless hypodermic injector.

2. Discussion of the Prior Art

As discussed in the Lindmayer et al U.S. Pat. No. 4,342,310, issued on Aug. 3, 1982, and in U.S. patent application Ser. No. 485,046, filed April 14, 1983, the needleless injection of medicines into the body is decidedly preferable to injection by means of skin piercing needles. A needleless injector makes a substantially smaller hole than a needle, and consequently is less painful and results in less damage than the needle. However, needleless injectors have only recently begun to achieve public acceptance. A basic reason for the limited use of such injectors is the difficulties and inconvenience involved in injecting different medicines using the same injector. Until now, it was necessary to sterilize an injector used to inject one medicine before using the same injector for injecting another medicine. Sterilization was necessary to purge the contaminating first medicine. Accordingly, for the most part, the use of needleless injectors has been limited to mass inoculations or other situations, e.g. the administration of steroids local anaesthetics or insulin in which the type of medicine is not changed frequently.

Thus, it is readily apparent that a need exists for a device which permits the extension of needleless injection to situations in which a variety of medicines are injected into successive patients.

A search of the relevant patent literature reveals that others are aware of the problem, and that attempts have been made to solve such problem. In this connection, reference is made to Canadian Pat. No. 569,887, issued to R. P. Scherer on Feb. 3, 1969, U.S. Pat. No. 2,635,601 issued to E. A. May on April 21, 1953; U.S. Pat. No. 2,764,977, issued to G. W. Ferguson on Oct. 2, 1956; U.S. Pat. No. 3,688,765, issued to J. S. Gasaway on Sept. 5, 1972; U.S. Pat. No. 4,089,334, issued to P. R. Schwebel et al on May 16, 1978; and U.S. Pat. No. 4,124,024, issued to P. R. Schwebel et al on Nov. 7, 1978. Each of these patents describes an injector which utilizes a disposable ampoule or cartridge containing a single dosage of medicine. Such devices are unsatisfactory, because it must be possible to adjust the dosage of most medicines. The dosage required for any individual is determined, inter alia, by the age and weight of the individual, and the stage of the illness. Thus, the person administering the medicine must be able to vary the dosage. The production and storage of a large number of ampoules or cartridges containing a variety of dosages of many medicines would be prohibitively expensive and impractical.

The O. H. Banker U.S. Pat. Nos. 3,292,621 and 3,292,622 issued on Dec. 20, 1966 teach the use of an adjustable stroke injection device and an adjustable unit, respectively. With the first of the Banker devices, some medicine may remain in the ampoules which can be quite expensive. Moreover, there is no provision for filling of the device with different medicines. The other Banker unit must be sterilized if the medicine being administered is changed.

Accordingly, in spite of the extent of earlier work in this field, the need still exists for a simple disposable syringe which can be used for needleless inoculations. An object of the present invention is to attempt to meet such need by providing a disposable device, which eliminates the need for sterilization between uses of the injector.

At least one embodiment of the invention prevents the accidental re-use of a contaminated disposable syringe. Such re-use is possible with conventional disposable syringes. Moreover, the syringe of the present invention can be filled accurately to the required dosage, and, in one form, can be re-used for multiple injections, e.g. when injecting insulin for the treatment of a diabetic.

GENERAL DESCRIPTION OF THE INVENTION

Accordingly, the present invention relates to a disposable syringe for use in a needleless injector of the type including a casing, a piston slidably mounted in the casing for movement between a retracted position and an extended position, and drive means for driving the piston from the retracted to the extended position, the syringe comprising tubular plastic barrel means, said barrel means having an open rear end for insertion into said casing and a closed front end for extending out of said casing; orifice means in said front end of said barrel means for admitting medicine into said barrel means, plastic plunger means slidably mounted in said barrel means, a rear end of said plunger means extending out of said open rear end of said barrel means for gripping whereby the plunger means can be moved away from said closed front end of said barrel means to a loaded position in which medicine fills the space in said barrel means between said closed front end and the front end of said plunger means, said rear end of the plunger means being engageable by said piston, whereby the plunger means can be moved from the loaded position to a discharge position against said closed front end of the barrel means to discharge substantially all of the medicine from said barrel means.

In this description and in the appended claims, the term "front" is used to identify the medicine receiving and injection end of the barrel or plunger, and the term "rear" is used to identify the other end of the barrel or plunger.

BRIEF DESCRIPTION OF THE DRAWINGS

The invention will now be described in greater detail with reference to the accompanying drawings, which illustrate preferred embodiments of the invention, and wherein:

FIG. 1 is a schematic side elevation view of one embodiment of the disposable syringe of the present invention;

FIG. 2 is a longitudinal sectional view of the syringe of FIG. 1;

FIG. 3 is a front end view of the syringe of FIGS. 1 and 2;

FIG. 4 is a rear end view of the syringe of FIGS. 1 to 3;

FIG. 5 is a longitudinal sectional view of the second embodiment of the syringe of the present invention;

FIG. 7 is a partly sectioned, side elevation view of a second type of needleless injector containing a third embodiment of the syringe of the present invention; and FIG. 8 is a longitudinal sectional view of the other end of the injector and syringe of FIG. 7.

DESCRIPTION OF PREFERRED EMBODIMENTS

Figure 6:
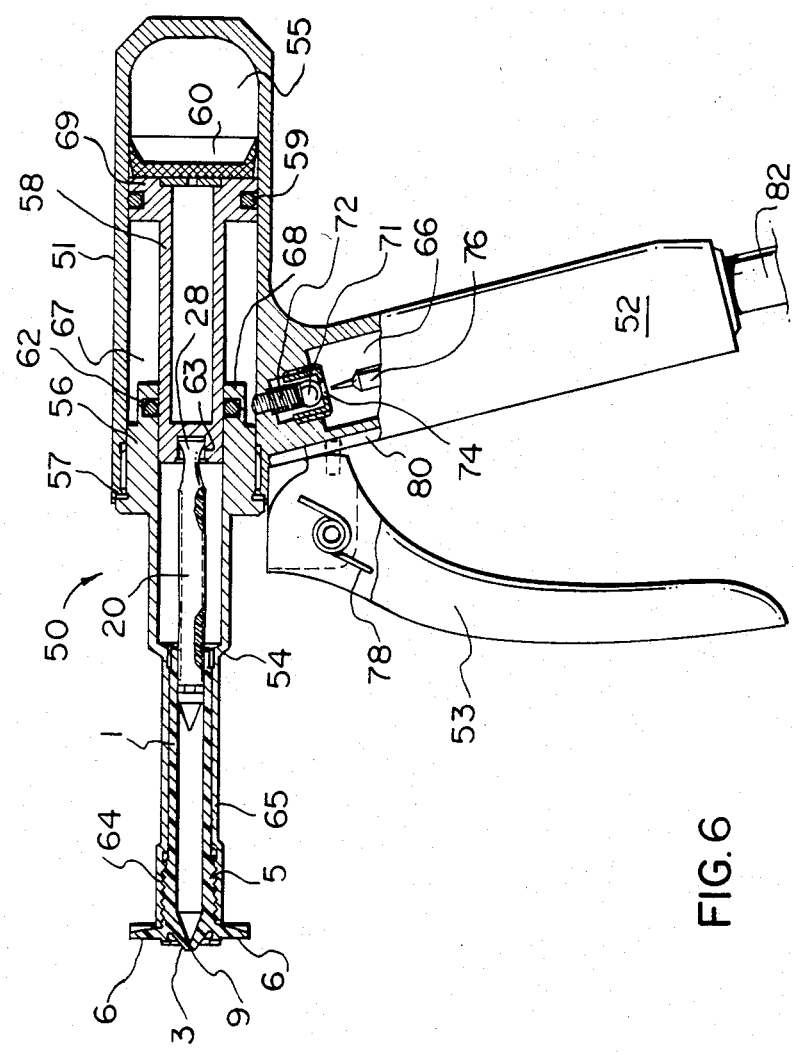
FIG. 6 is a partly sectioned, side elevation view of the syringe of FIGS. 1 to 4 in a needleless injector.

With reference to FIGS. 1 to 4, one embodiment of the syringe of the present invention includes a tubular barrel generally indicated at 1 and a plunger generally indicated at 2. The barrel 1 is defined by a hollow cylindrical body. The body may taper slightly from a closed front end 3 to an open rear end 4. The dimensions of a tapered body need not be as exact as those of a cylindrical body. The barrel 1 is formed of a transparent, plastic material, e.g. polypropylene of the type used in the barrel of conventional, commercially available disposable syringes. The plunger 2 is formed of a hard plastic.

External threads 5 are provided on the front end 3 of the barrel 1 for mounting the latter in an injector, as described in greater detail hereinafter. It will be appreciated that the threads can be replaced by a bayonet or other type coupling. A pair of diametrically opposed wings 6 extend radially outwardly the front end 3 of the barrel 1 for facilitating manual rotation of the barrel 1 during insertion or removal of the barrel from an injector. A conical nose 8 at the centre of the front end 3 of the barrel contains a longitudinally extending injection orifice 9. A separable needle 10 extends forwardly from the nose 8 for loading or filling of the syringe. For such purpose, an annular groove 11 is provided at the junction between the rear end of the needle 10 to render the needle 10 frangible. A cylindrical cap 14 normally protects the needle 10 and the front injection end of the syringe. The open end of the cap 14 includes an annular bead 15, which is retained in an annular recess 16 at the base of the nose 8. Sawtooth projections 18 are provided on the front end of the barrel 1 for preventing slipping of the syringe on the skin of a patient. A longitudinally extending, smooth bottomed slot 19 is provided on each side of the barrel 1. The slot 19 extends from between the projections 18 to the rear end of the threads 5, so that the interior of the front end 3 of the barrel can easily be seen from the outside.

The plunger 2 includes a cylindrical body 20 with a conical front end 21 for abutting the conical interior end 22 of the barrel 1. The use of mating conical surfaces 21 and 22 ensures that virtually all of the medicine contained in the chamber 24 is discharged when the plunger is moved from the rear or loaded position (FIGS. 1 and 2) to the front or discharge position (FIG. 5). An O-ring 25 provides a fluid-tight seal between the front end of the plunger 2 and the barrel 1. A pair of concave depressions 27 are provided near the rear end 28 of the body 20 to facilitate gripping of the plunger 2 during filling. The rear end 28 of the body 20 is protected by a cylindrical cap 30 until the syringe is about to be used.

Transversely extending lines 32 are provided on the body 20 for indicating the dosage in the chamber 24. The lines 32 are visible through a rectangular slot 33 in the side of the reduced diameter rear end 4 of the barrel 1. A line 35 on one side of the slot 33 provides an accurate reading of the volume of medicine (dosage) in the chamber 24. A pair of opposed rectangular grooves 36 extend along substantially the entire length of the body 20. The bottom 37 of each groove 36 has a sawtooth configuration. Small ridges 38 on opposed projections 39 in the rear end 4 of the barrel 1, engage the teeth in the grooves 36. Thus, as the plunger 2 is moved rearwardly in the barrel 1 and medicine is drawn into the barrel, and the ridges 38 make a clicking sound as they move over the teeth in the grooves 36. The teeth correspond to the lines 32, so that blind patients such as diabetics can measure the dosage by counting the clicks. Moreover, this arrangement prevents rotation of the plunger relative to the barrel.

The syringe of FIGS. 1 to 4 is loaded by inserting the needle 10 into a medicine bottle 40 (FIG. 5) and withdrawing the plunger 2. The syringe of FIG. 5 is the same as that of FIGS. 1 to 4, except that the front end includes a frusto-conical projection 42, which has the same taper as the funnel 43 of a conventional disposable needle 44. The projection 42 contains an insert 45, with the injection orifice 46 therein. A recess 47 around the projection 42 includes a thread 48 for securing the flanged end 49 of the needle funnel 43. The end 49 of the funnel 43 is inserted into the recess 47 and rotated to lock the needle in place. The needle 44 is then inserted into the medicine bottle 40, and the plunger 2 is partially withdrawn to fill the barrel 1.

The syringe of FIGS. 1 to 4 or 5 can be used in a variety of injectors including the injector indicated generally at 50 in FIG. 6. The injector 50 is similar to the injector described in U.S. Pat. No. 4,342,310 mentioned hereinbefore, and includes an elongated tubular casing 51 with a handle 52 and a trigger 53 substantially perpendicular thereto. A tubular barrel 54 is connected to the front end of the casing 51. The rear end of the casing 51 defines a compression chamber 55, which contains a substance such as chlorotrifluoromethane which changes to a liquid when subjected to pressure at normal room temperature, and changes back to a gas when the pressure is released. There is sufficient of the substance in the chamber 55 that some liquid is always present in such chamber.

The rear end 56 of the barrel 54 is threaded for connecting the barrel 54 to the casing 51. A gasket 57 provides a fluid-tight seal between the barrel 54 and the casing 51. A piston 58 is slidably mounted in the compression chamber 55 for longitudinal reciprocating movement between a rest position and a charged position (FIG. 6) in which the piston 58 compresses the gas to convert at least a portion of the gas into a liquid. An O-ring 59 seals the piston 58 with respect to the interior of the handle end of the casing 51. A gasket 60 on the rear, compressions chamber end of the piston 58 seals the chamber 55 from the remainder of the casing 51.

The piston 58 is slidably mounted in the rear end of the barrel 54. An O-ring 62 provides a seal between the piston 58 and the barrel 54. A recess 63 is provided in the front end of the piston 58 for receiving the rear end 28 of the plunger 20. The front end 64 of the barrel 54 is internally threaded, so that the barrel 1 of the disposable syringe can be securely mounted in such barrel 54. In order to use a thin walled barrel 1 which is capable of resisting the high pressures required in the barrel 54 to create a high velocity jet, the front section 65 of the barrel 54 is tapered internally to match the taper of the syringe barrel 1.

The handle 52 of the injector contains a charging chamber 66 for a liquid such as an oil. The chamber 66 can be connected to a pressure chamber 67 between the rear end 68 of the barrel 54 and the rear end 69 of the piston 58. When the piston 58 moves into the chamber 55, the pressure chamber 67 enlarges to receive liquid from the charging chamber 66. Liquid from the chamber 66 passes through a valve defined by a ball 71 and a helical spring 72, which biases the ball against a seat 74.

A rod 76 is slidably mounted in the chamber 66 for moving the ball 71 upwardly to open the valve. The bottom end of the rod 76 is connected to a piston (not shown), which is operated by the trigger 53. Because the piston actuating mechanism does not form part of the present invention, no details of such mechanism are provided herein. It is sufficient to know that the rod 76 is moved by operation of the trigger 53, which is pivotally connected to the casing 51. The trigger 53 is biased away from the handle 52 by a spring 78. The trigger 53 is connected to a bar 80, which is slidably mounted in a slot in the front side of the handle 52. The bottom end of the bar 80 (not shown) operates the piston to move the rod 76 against the ball 71. In order to move the piston 58 rearwardly to the cocked position, it is necessary to pump the trigger 53 which pumps liquid from the charging chamber 66 into the pressure chamber 67. Thus, the gas in the compression chamber 55 is compressed and changes into liquid form. In order to administer medicine, the front end 3 of the barrel 1 is placed against the skin, and a safety catch 82 on the bottom end of the handle 52 is rotates 90° to connect the trigger 53 to the rod 76, releasing the ball 71 when the trigger is pressed. In the manner the piston 58 is released, and moves forward in the barrel 54, the plunger 20 moves forward in the barrel 1 to discharge the medicine, and the charging liquid returns to the handle 52.

The disposable syringe of the present invention can also be used with a needleless injector of the type disclosed by Canadian patent application No. 403,840, also mentioned hereinbefore. Referring to FIGS. 7 and 8, the injector includes a casing generally indicated at 84. The casing 84 is defined by cylindrical, telescoping front and rear sections 85 and 86, respectively. The rear section 86 of the casing 84 is mounted in the front section 85 for movement between the extended or rest position (FIG. 7) and the retracted position (FIG. 8). The front section 85 of the casing 84 includes a forwardly extending neck 87 and an internal cylinder 88 for receiving a syringe in accordance with the present invention. For such purpose, the front end 89 of the cylinder 88 is internally threaded for retaining the externally threaded front end 90 of the barrel 91 of the syringe.

During injection, the front end 90 of the barrel 91 is covered by an injection head 92. The head 92 includes a cylindrical outer sleeve 93, which surrounds the neck 87 of the casing 84 and an externally threaded inner sleeve 94 for connecting the head 92 to the front end 89 of the cylinder 88. Projections 95 are provided on the disc-shaped front end 96 of the head 92 for preventing slipping of the injector on the skin during use. An insert 97 with an injection orifice 98 is provided in the front end 96 of the head 92.

As in the other embodiments of the invention, a plunger 100 is slidably mounted in the barrel 91 for movement between a front, rest or discharge position (FIG. 7) and a loaded or filled position (FIG. 8). The plunger 100 includes a tapered front end 101 and is sealed in the barrel 91 by an O-ring 102. The rear end of the cylinder 88 carrying the syringe is externally threaded for mounting in an internally threaded ring 103, which is connected to an annular, inwardly extending shoulder 104 on the front end of the rear casing section 86. Rotation of the rear casing section 86 with respect to the section 85 causes movement of the section 86 into the section 85. Such movement of the rear section 86 into the front section 85 of the casing is limited by a latch mechanism. The latch mechanism includes a hole 105 and a ball 106 in the rear casing section 86. When the ball 106 is aligned with the hole 105, the ball is forced into the hole 105 by a stepped collar 107. The collar 107 and the ball 106 are mounted in a cup-shaped bushing 108, which is slidable in the rear casing section 86. A helical spring 110 in the collar 107 biases the collar and the ball 106 towards the rear of the casing section 86. In the extended position of the casing 84 (FIG. 7), the ball 106 bears against the interior surface 112 of the casing section 86. When the ball 106 becomes aligned with the hole 105, the ball is pushed into the hole.

When the casing sections 85 and 86 move together a stack of disc springs 113 is compressed between the bushing 108 and an end cap 114 on the casing 84. The cap 114 is cup-shaped and externally threaded for mounting in the internally threaded end 115 of the casing section 86. Opposed rectangular wings 116 are provided near the end 115 of the casing section 86 to facilitate rotation of the section 86. The injector is actuated, i.e. the bushing 108 is pushed forwardly by the springs 113, when the sections 85 and 86 are released by a push button (not shown) in the cap 114. As described in Canadian patent application No. 403,840, the desired injection pressure can be achieved by providing the appropriate disc springs 113 in series.

In order to move the plunger 100 with the bushing 108, the rear end 117 of the plunger 100 is bifurcated for engaging the bushing 108. An annular flange or washer 118 on the plunger 100 moves the bushing 108 rearwardly to engage the springs 113 when the syringe is inserted into the casing 84. The rear casing section 86 is rotated counterclockwise to move the front section 85 and the barrel 91 away from the rear section 86. As the casing sections 85 and 86 move apart, the plunger 100 initially moves the barrel 91 because of the friction of the O-ring 102. The enlarged heads 119 on the arms at the rear end 117 of the plunger 100 engage the rear surface of the bushing 108 to prevent movement of the plunger 100 with the barrel 91. Continued separation of the casing sections 85 and 86 creates a partial vacuum in a chamber 120 (FIG. 8) in the syringe for receiving medicine.

When filling the syringe, the injection head 92 is removed, and a bottle holder generally indicated at 122 is placed in the front end 87 of the casing 84. The bottle holder 122 includes a hollow cylindrical body 123 with an open bottom end 124 for receiving a standard medicine bottle 125. Longitudinally extending slots 126 in a skirt portion 127 of the body 123 facilitate insertion of the bottle 125 into the holder by making the body flexible. A needle 128 extends downwardly from the closed top end 129 of the holder for puncturing the top end of the medicine bottle 125. An externally threaded sleeve 130 extends upwardly from the top end 129 of the holder for connecting the holder to the front end 89 of the cylinder 88. In such position, the sleeve 130 receives a projection 131 on the front end of the barrel 91 ensuring proper filling of the chamber 20.

This embodiment of the invention is best adapted for the treatment of diabetics, who generally use one type of medicine only. Injections can be repeated using the same barrel 91 until such barrel becomes contaminated at which time the disposable head 92, the barrel 91 and the plunger 100 are replaced with sterile elements.

All of the elements of each embodiment of the invention are stored in hermetically sealed, sterile plastic bags of the type used for conventional disposable syringes. The syringe of the present invention provides a relatively inexpensive, quick means for sterile injections, without the inconvenience of sterilization. Moreover, the syringe described hereinbefore is relatively accurate in terms of dosage, and can be filled from virtually any bottle or vial.

We claim:

1. A disposable syringe for use in a needleless injector of the type including a casing, a piston slidably mounted in the casing for movement between a retracted position and an extended position, and drive means for driving the piston from the retracted to the extended position, the syringe comprising tubular plastic barrel means, said barrel means having an open inner end for insertion into said casing and a closed outer end for extending out of said casing; connector means for releasably retaining said barrel means in said casing; orifice means in said closed end of said barrel means for admitting medicine into said barrel means, plunger means slidably mounted in said barrel means, one end of said plunger means extending out of said open inner end of said barrel means for gripping whereby the plunger means can be moved away from said closed outer end of said barrel means to a loaded position in which medicine fills the space in said barrel means between said closed outer end and the other end of said plunger means, said one end of the plunger means being engageable by said piston, whereby the plunger means can be moved from the loaded position to a discharge position against said closed outer end of the barrel means to discharge substantially all of the medicine from said barrel means.

2. A syringe according to claim 1, wherein said barrel means and plunger means are tapered slightly from front to rear for insertion into a similarly tapered casing.

3. A syringe according to claim 1, wherein the interior of the front end of said barrel means adjacent said orifice means is substantially conical, and said front end of said plunger means is similarly substantially conical for ensuring the discharge of substantially all medicine from said barrel means.

4. A syringe according to claim 1, including needle means detachably connected to the front end of said barrel means for use in loading the syringe.

5. A syringe according to claim 4, wherein said needle means is integral with said barrel means and contiguous with said orifice means.

6. A syringe according to claim 1, wherein said connector means includes threads on the outer front end of said barrel means for connecting said barrel means to an internally threaded casing.

7. A syringe according to claim 6, including wing means on the front end of said barrel means facilitating mounting of said barrel means in a casing.

8. A syringe according to claim 1, 2 or 3, including teeth means on the front end of said barrel means around said orifice means for preventing slipping of said barrel means on the skin of a user.

9. A syringe according to claim 1, including rack means extending longitudinally of said plunger means; and a projection on said barrel means for engaging said rack means to provide an indication of movement of said plunger means relative to said barrel means.

10. A syringe according to claim 1, including nozzle means extending outwardly from the front end of said barrel means, said nozzle means containing said orifice means and being adapted to matingly engage a needle funnel to facilitate loading of the syringe.

11. A syringe according to claim 1, including disposable head means for mounting on said front end of said barrel means; inset means in said head means; and an injection orifice in said insert means for alignment with said orifice means in said barrel means.

12. A syringe according to claim 1, wherein said connector means includes a bayonet connector at the outer front end of said barrel means for connecting said barrel means to said casing.

* * * * *